US012690999B2

(12) United States Patent
Kuczek et al.

(10) Patent No.: US 12,690,999 B2
(45) Date of Patent: Jul. 28, 2026

(54) INTEGRATED PRESSURE REGULATOR AND EJECTOR PUMP FOR URINARY RELIEF SYSTEM

(71) Applicant: B/E Aerospace, Inc., Winston Salem, NC (US)

(72) Inventors: Andrzej E. Kuczek, Bristol, CT (US); Yasmin Khakpour, South Windsor, CT (US); Matthew R. Pearson, Hartford, CT (US)

(73) Assignee: B/E AEROSPACE, INC., Winston Salem, NC (US)

( * ) Notice: Subject to any disclaimer, the term of this patent is extended or adjusted under 35 U.S.C. 154(b) by 528 days.

(21) Appl. No.: 18/123,182

(22) Filed: Mar. 17, 2023

(65) Prior Publication Data

US 2024/0307213 A1     Sep. 19, 2024

(51) Int. Cl.
*A61F 5/455*       (2006.01)
*A61F 5/44*        (2006.01)

(52) U.S. Cl.
CPC ............ *A61F 5/455* (2013.01); *A61F 5/4405* (2013.01)

(58) Field of Classification Search
CPC .............. A61M 25/0017; A61M 39/22; A61M 25/0075; A61M 2025/0078; A61M 2205/50; A61M 2205/3334; A61M 2202/0496; A61M 2039/226; A61M 2206/10; A61M 2205/3331; A61M 2230/005; A61M 16/024; A61M 2016/0027; A61M 2205/3327; A61M 2205/3344; A61M 1/1086; A61M 2205/3337; A61M 2005/3123; A61M 25/0082; A61M 5/16877; A61M 5/16881; A61M 5/16886; A61F 5/44; A61F 5/455; (Continued)

(56) References Cited

U.S. PATENT DOCUMENTS 3,870,072 A * 3/1975 Lindemann ......... A61M 13/003
                                                    600/101
5,662,631 A    9/1997 Marx
                      (Continued)

FOREIGN PATENT DOCUMENTS

EP          3977967          4/2022

OTHER PUBLICATIONS

European Patent Office, European Search Report dated Jul. 15, 2024 in Application No. 24155102.7.

*Primary Examiner* — Guy K Townsend
*Assistant Examiner* — Alessandro R Del Priore
(74) *Attorney, Agent, or Firm* — SNELL & WILMER L.L.P.

(57)                ABSTRACT

A control unit for a urinary relief system is disclosed herein. The control unit includes a pressure regulator having a high pressure inlet and a reduced pressure outlet, the high pressure inlet having a first air pressure, and the reduced pressure outlet having a second air pressure, an ejector having an pressurized air input, a vacuum port, and an air output, the pressurized air input of the ejector coupled to the reduced pressure outlet of the pressure regulator and the vacuum port connected to a storage device, an ejector head housing the pressure regulator and the ejector, and a pressurized gas source coupled to the high pressure inlet of the pressure regulator, the pressurized gas source providing an air flow having the first air pressure.

20 Claims, 5 Drawing Sheets

(58) Field of Classification Search
CPC .... A61F 5/4405; A61F 5/451; A61F 13/0283; A61F 2013/0296; A61F 2/042; A61B 10/007; A61B 5/4839; A61B 5/0022; A61B 5/14542; A61B 5/4845; A61B 5/4848; A61B 10/0051; A61B 5/0064; A61B 5/0205; A61B 5/024; A61B 5/02416; A61B 5/0806; A61B 5/14551; A61B 5/6801; A61B 5/6816; A61B 5/6823; A61B 5/6826; A61B 5/6829; A61B 5/6898; A61B 5/7203; A61B 5/7405; A61B 5/746; A61B 5/747; A61B 5/748; A61B 7/003; A61B 17/00234; A61B 17/3403; A61B 2017/3413; A61B 2217/005; A61B 2560/0214; A61B 5/002; A61B 5/01; A61B 5/087; A61B 10/00; A61B 10/0045; A61B 17/0218; A61B 17/22004; A61B 17/24; A61B 17/3421; A61B 17/3474; A61B 17/8805; A61B 2010/0006; A61B 2010/0009; A61B 2017/00738; A61B 2017/246; A61B 2017/345; A61B 2034/107; A61B 2034/2046; A61B 2034/301; A61B 2050/185; A61B 2503/40; A61B 2560/0219; A61B 2560/04; A61B 2560/0462; A61B 2562/0233; A61B 2562/0247; A61B 2562/0271; A61B 34/10; A61B 34/20; A61B 34/25; A61B 34/32; A61B 34/70; A61B 34/76; A61B 50/13; A61B 50/18; A61B 5/0002; A61B 5/0026; A61B 5/0031; A61B 5/02055; A61B 5/0215; A61B 5/02154; A61B 5/02158; A61B 5/029; A61B 5/03; A61B 5/04286; A61B 5/044; A61B 5/046; A61B 5/04882; A61B 5/05; A61B 5/14539; A61B 5/14546; A61B 5/14557; A61B 5/204; A61B 5/208; A61B 5/4064; A61B 5/4343; A61B 5/4833; A61B 5/6852; A61B 5/6866; A61B 5/7264; A61B 5/742; A61B 8/065; A61B 90/361; B64D 10/00; G16H 40/63; G16H 10/60; G16H 20/17; G16H 40/67; G16H 20/13; G16H 15/00; G16H 20/10; G16H 20/40; G16H 40/60; G08B 21/0415; G08B 21/0469; G08B 21/0476; G08B 21/0492; G08B 3/10; G08B 5/22; G06F 19/00; G06F 3/04817; G06F 19/3456; G06F 19/3462; G06F 21/31; G06F 3/0482; G06F 3/04847; G06F 3/04883; G06F 3/167; A61J 1/1406; A61J 1/20; A61J 1/2024; F16K 3/03; G06Q 10/087; G06Q 20/10; G06Q 50/22
See application file for complete search history.

(56) References Cited

U.S. PATENT DOCUMENTS

| | | | |
|---|---|---|---|
| 5,678,564 A | 10/1997 | Lawrence et al. | |
| 7,135,012 B2 | 11/2006 | Harvie | |
| 7,448,288 B2 | 11/2008 | Montefusco | |
| 2004/0176746 A1 | 9/2004 | Forral | |
| 2009/0030383 A1* | 1/2009 | Larsen | A61M 1/743 |
| | | | 604/315 |
| 2020/0054800 A1* | 2/2020 | Wilbourn | A61M 25/0017 |
| 2021/0228795 A1 | 7/2021 | Hughett et al. | |
| 2022/0104965 A1 | 4/2022 | Vaninetti et al. | |

* cited by examiner

1

INTEGRATED PRESSURE REGULATOR AND EJECTOR PUMP FOR URINARY RELIEF SYSTEM

GOVERNMENT LICENSE RIGHTS

This disclosure was made with government support under contract No. FA8606-22-9-0002 awarded by the United States Air Force. The government has certain rights in the disclosure.

FIELD

The present disclosure generally relates urinary relief systems, and more specifically, to pressurized urinary relief systems for pilots.

BACKGROUND

Aircrew often need to urinate multiple times during flights without removing restraint systems and flight equipment. Current mission profiles and air refueling abilities have led to longer flight times for aircrew. As a result, some aircrew, especially female aircrew, resort to ingesting fewer liquids to reduce the need to urinate, resulting in dehydration. A safe, reliable, and effective system to provide aircrew, especially female aircrew, the capability of bladder relief during flight is sought.

SUMMARY

A control unit for a urinary relief system is disclosed herein. The control unit includes a pressure regulator having a high pressure inlet and a reduced pressure outlet, the high pressure inlet having a first air pressure, and the reduced pressure outlet having a second air pressure, an ejector having an pressurized air input, an vacuum port, and an air output, the pressurized air input of the ejector coupled to the reduced pressure outlet of the pressure regulator and the vacuum port connected to a storage device, an ejector head housing the pressure regulator and the ejector, and a pressurized gas source coupled to the high pressure inlet of the pressure regulator, the pressurized gas source providing an air flow having the first air pressure.

In various embodiments, the second air pressure is about 25 times less than the first air pressure to about 35 times less than the first air pressure. In various embodiments, the control unit further includes a valve disposed between the pressurized gas source and the pressure regulator, the valve configured to pass a gas from the pressurized gas source to the pressure regulator.

In various embodiments, the control unit further includes a toggle coupled to the valve, the toggle configured to activate the valve to release the gas from the pressurized gas source.

In various embodiments, the toggle is further configured to deactivate the valve, stopping the release of the gas from the pressurized gas source. In various embodiments, the pressurized gas source includes one or more $CO_2$ cartridges. In various embodiments, the control unit further includes one or more valves, each of the one or more valves being disposed between each $CO_2$ cartridge of the one or more $CO_2$ cartridges and the pressure regulator, each valve configured to pass pressurized $CO_2$ from each $CO_2$ cartridge to the pressurized gas source.

Also disclosed herein is a urinary relief system including a human interface device, a storage device coupled to the human interface device, and a control unit coupled to the storage device. The control unit includes a pressure regulator having a high pressure inlet and a reduced pressure outlet, the high pressure inlet having a first air pressure, and the reduced pressure outlet has a second air pressure, an ejector having an pressurized air input, an vacuum port, and an air output, the pressurized air input of the ejector coupled to the reduced pressure outlet of the pressure regulator and the vacuum port connected to the storage device, an ejector head housing the pressure regulator and the ejector, and a pressurized gas source coupled to the high pressure inlet of the pressure regulator, the pressurized gas source providing an air flow having the first air pressure.

In various embodiments, the control unit further includes an air inlet port coupled to the ejector and to the storage device and an air outlet port coupled to the ejector. In various embodiments, the control unit further includes a fast release connector having a first port and a second port, the fast release connector configured to removably coupled to the ejector head housing such that the first port is coupled to the air inlet port and the second port is coupled to the air outlet port.

In various embodiments, the second air pressure is about 30 times less than the first air pressure. In various embodiments, the control unit further includes a pressurized gas housing to house the pressurized gas source, the pressurized gas housing configured to be removably coupled to the ejector head housing. In various embodiments, the control unit further includes a valve disposed between the pressurized gas source and the pressure regulator, the valve configured to pass a gas from the pressurized gas source to the pressure regulator. In various embodiments, the pressurized gas source includes one or more $CO_2$ cartridges.

Also disclosed herein is a urinary relief system including a human interface device, a storage device coupled to the human interface device, and a control unit coupled to the storage device. The control unit includes an ejector head housing having an air inlet port and an air outlet port, the air inlet port coupled to the storage device, a first pressurized gas housing removably coupled to the ejector head housing, a first pressurized gas source disposed in the first pressurized gas housing, a pressure regulator disposed in the ejector head housing, the pressure regulator coupled to the first pressurized gas source, and an ejector coupled to the pressure regulator, the air inlet port, and the air outlet port.

In various embodiments, the pressure regulator includes a high pressure inlet receiving a gas having a first pressure and a reduced pressure outlet outputting the gas having a second pressure that is less than the first pressure. In various embodiments, the second pressure is about 15 times less than the first pressure to about 45 times less than the first pressure. In various embodiments, the urinary relief system further includes a second pressurized gas housing removably coupled to the first pressurized gas housing and a second pressurized gas source disposed in the second pressurized gas housing.

In various embodiments, the first pressurized gas housing further includes a first valve coupled to the first pressurized gas source and to the pressure regulator when the first pressurized gas housing is coupled to the ejector head housing and a first toggle disposed on an outside surface of the first pressurized gas housing, the first toggle coupled to the first valve and configured to open the first valve in response to being toggled. In various embodiments, the first pressurized gas housing is configured to allow replacing the first pressurized gas source.

The foregoing features and elements may be combined in any combination, without exclusivity, unless expressly indicated herein otherwise. These features and elements as well as the operation of the disclosed embodiments will become more apparent in light of the following description and accompanying drawings.

BRIEF DESCRIPTION OF THE DRAWINGS

The subject matter of the present disclosure is particularly pointed out and distinctly claimed in the concluding portion of the specification. A more complete understanding of the present disclosure, however, may best be obtained by referring to the following detailed description and claims in connection with the following drawings. While the drawings illustrate various embodiments employing the principles described herein, the drawings do not limit the scope of the claims.

DETAILED DESCRIPTION

Figure 1A:
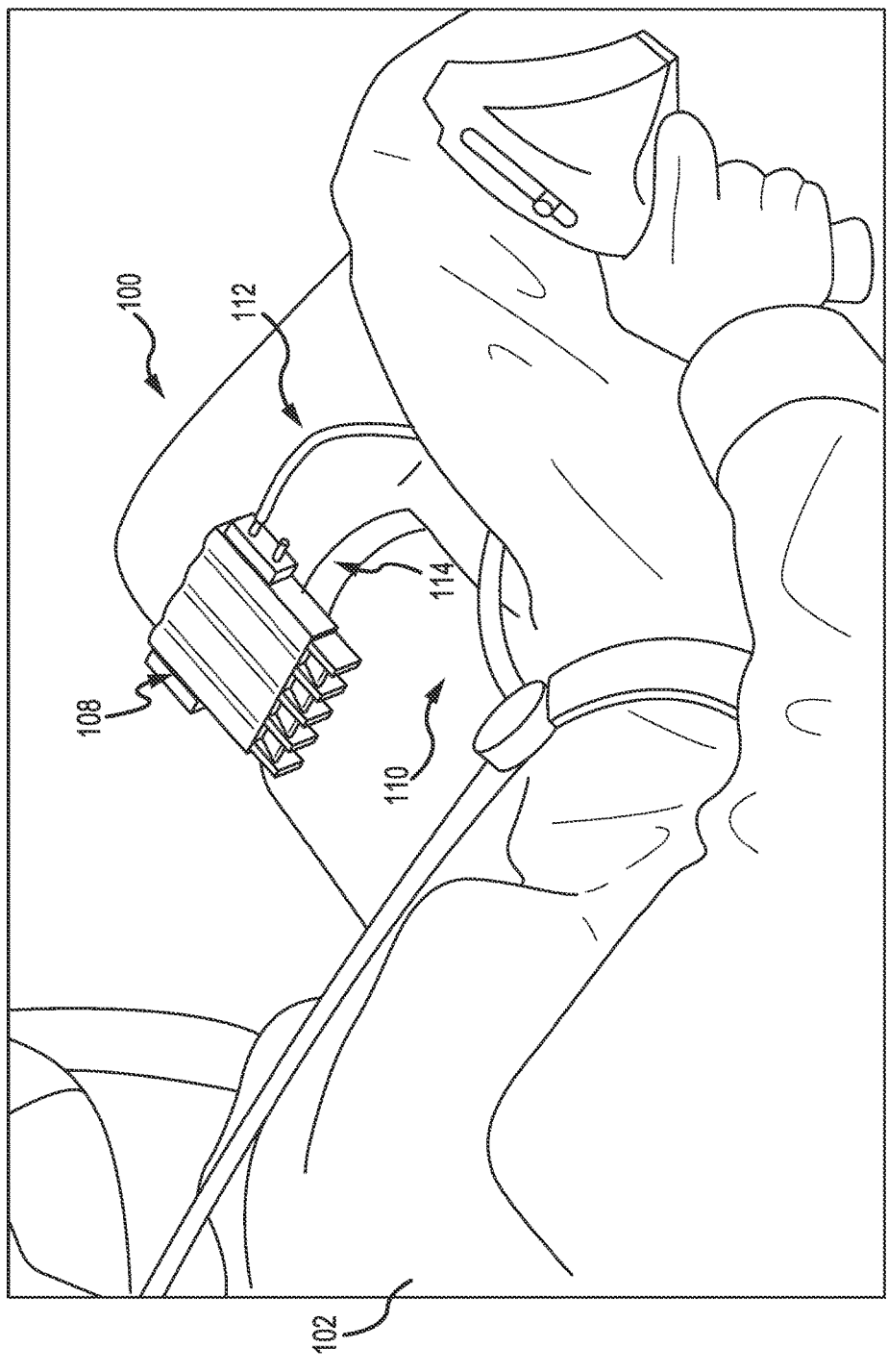
FIGS. 1A and 1B illustrate a urinary relief system, in accordance with various embodiments.

The following detailed description of various embodiments herein makes reference to the accompanying drawings, which show various embodiments by way of illustration. While these various embodiments are described in sufficient detail to enable those skilled in the art to practice the disclosure, it should be understood that other embodiments may be realized and that changes may be made without departing from the scope of the disclosure. Thus, the detailed description herein is presented for purposes of illustration only and not of limitation. While these exemplary embodiments are described in sufficient detail to enable those skilled in the art to practice the invention, it should be understood that other embodiments may be realized and that logical, chemical and mechanical changes may be made without departing from the spirit and scope of the invention. For example, the steps recited in any of the method or process descriptions may be executed in any order and are not necessarily limited to the order presented. Furthermore, any reference to singular includes plural embodiments, and any reference to more than one component or step may include a singular embodiment or step. Also, any reference to attached, fixed, connected, or the like may include permanent, removable, temporary, partial, full or any other possible attachment option. Additionally, any reference to without contact (or similar phrases) may also include reduced contact or minimal contact. It should also be understood that unless specifically stated otherwise, references to "a," "an" or "the" may include one or more than one and that reference to an item in the singular may also include the item in the plural. Further, all ranges may include upper and lower values and all ranges and ratio limits disclosed herein may be combined.

Disclosed herein is a urinary relief system including a human interface, a storage unit, and a control unit. The human interface is configured to collect and pass a liquid (e.g., urine) from a user (e.g., a pilot) to the storage unit. In various embodiments, the human interface may be designed to be worn under clothing (e.g., flight suit) and close the body of the user. In various embodiments, the huma interface may be fluidly coupled to the storage unit by a hose and, in some embodiments, a quick connector coupling. The storage unit is configured to collect and store the liquid (e.g., urine). In various embodiments, the storage unit includes an absorbent material configured to store the liquid. The various embodiments, the storage unit includes an input fluidly coupled to the human interface device and an output fluidly coupled to the control unit. In various embodiments, the output includes liquid restrictor so that no liquid is passed to the control unit. In various embodiments, the storage unit and the control unit may be coupled by a hose and, in various embodiments, a quick connector coupling.

In various embodiments, the control unit includes an ejector head having an integrated pressure regulator and ejector pump. In various embodiments, the control unit includes an ejector head housing and a $CO_2$ cartridge housing that are removably coupled to each other. In various embodiments, the control unit includes one or more air ejector pumps driven by one or more $CO_2$ cartridges. In various embodiments, the control unit further includes one or more pressure regulators between the $CO_2$ cartridges and the one or more ejector pumps. In various embodiments, the control unit includes a single housing that encloses the one or more ejector pumps, the one or more pressure regulators, and the one or more $CO_2$ cartridges. In various embodiments, the control unit may be modular allowing the user to add or remove sections to store $CO_2$ cartridges without impacting the performance of the control unit.

In various embodiments, the control unit provides suction to draw the liquid (e.g., urine) from the human interface into the storage unit. In various embodiments, the one or more pressure regulators reduces the working pressure of the control unit by up to 30 times the pressure of each $CO_2$ cartridge. In various embodiments, the reduction in pressure may result in an increase to operation run time of the urinary relief system. In various embodiments, the size of the control unit is reduced by integrating the pressure regulator and the ejector into a single ejector head unit. The control until described herein in its various embodiments may provide a compact design, an extend performance time, a modular control unit, and/or lower cost of fabrication.

Figure 1B:
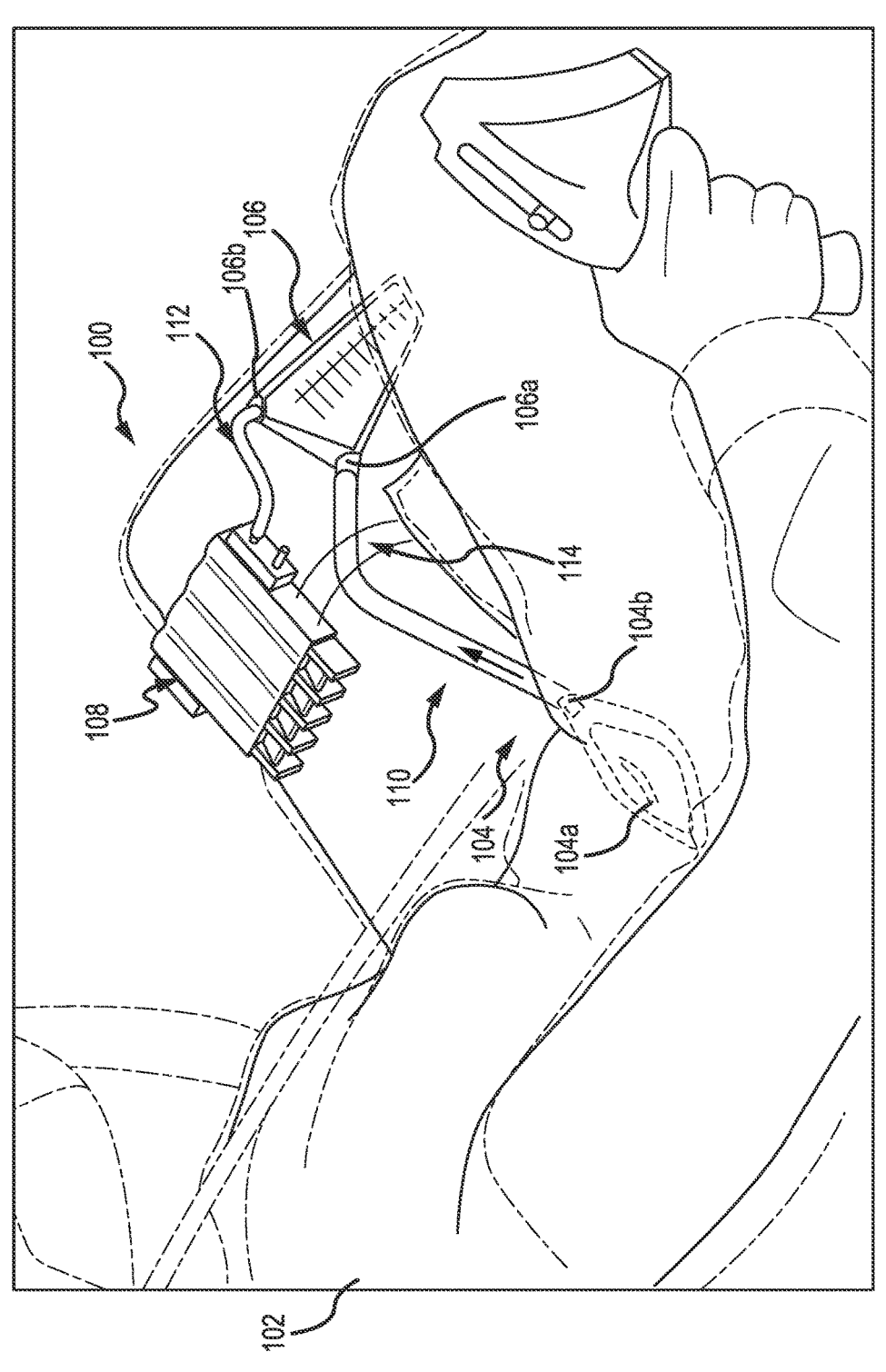

Referring to FIGS. 1A and 1B, a urinary relief system 100 for use by a pilot 102 (e.g., a female pilot) is illustrated, in accordance with various embodiments. Urinary relief system 100 includes a human interface device 104, a storage unit 106, and a control unit 108. Human interface device 104 is configured to be positioned under the clothing (e.g., flight suit, underwear, pants, etc.) and immediately adjacent the body of pilot 102 for use in flight. That is, between the body and clothing of pilot 102 when pilot 102 is in a seated position. In various embodiments, human interface device 104 may form a seal with the body of pilot 102. Human interface device 104 may be any size and/or shape conducive for placement under the clothing of pilot 102 and for collecting the liquid (e.g., urine) while in place. Human interface device 104 includes a collection portion 104a and an outlet port 104b.

Storage unit 106 includes a storage inlet port 106a and a storage outlet port 106b. Outlet port 104b of human interface device 104 is connected to storage inlet port 106a of storage unit 106 by an inlet hose 110 and storage outlet port 106b of storage unit 106 is connected to control unit 108 by an outlet hose 112. In various embodiments, storage unit 106 may be disposable. In various embodiments, control unit 108 and/or storage unit 106 may be secured to pilot 102 (e.g., secured to a leg) by one or more straps 114. Storage unit 106 is configured to receive and trap liquid (e.g., urine) received from storage inlet port 106a and not allow the liquid to exit through storage outlet port 106b.

Control unit 108 creates a motive force that draws the liquid (e.g., urine) from human interface device 104 and into storage unit 106. Air may be drawn, along with the liquid, into storage unit 106 by the vacuum created by control unit 108. In various embodiments, storage unit 106 includes a filter, or flow restrictor, that allows the air to exit storage unit 106 through storage outlet port 106b and keep the liquid secured in storage unit 106. In various embodiments, control unit 108 provides the motive force by creating a vacuum to draw the liquid from human interface device 104 to storage unit 106.

Figure 2:
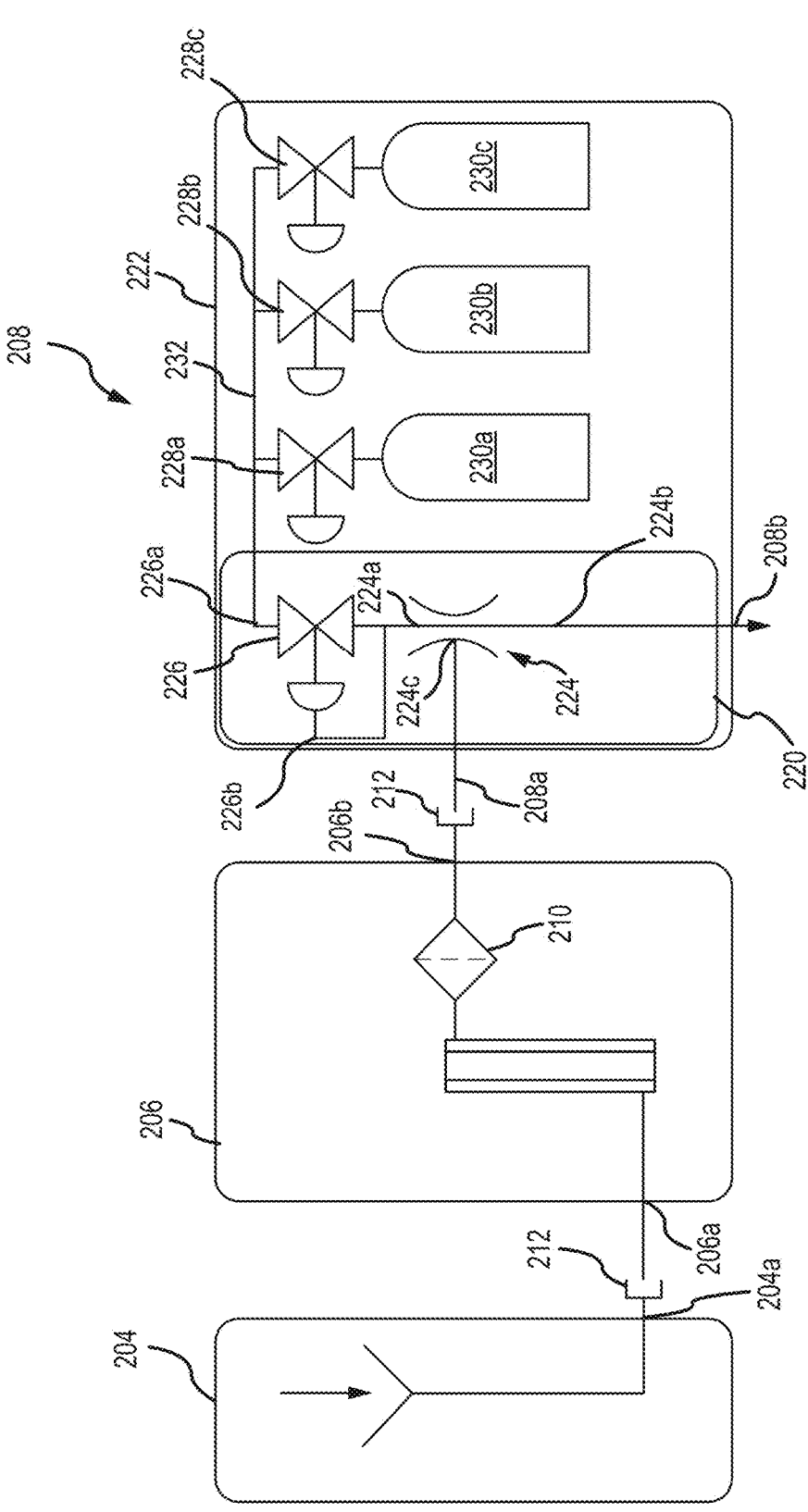
FIG. 2 illustrates a functional diagram of a urinary relief system, in accordance with various embodiments.
Figures 3A, 3B, 3C, 3D:
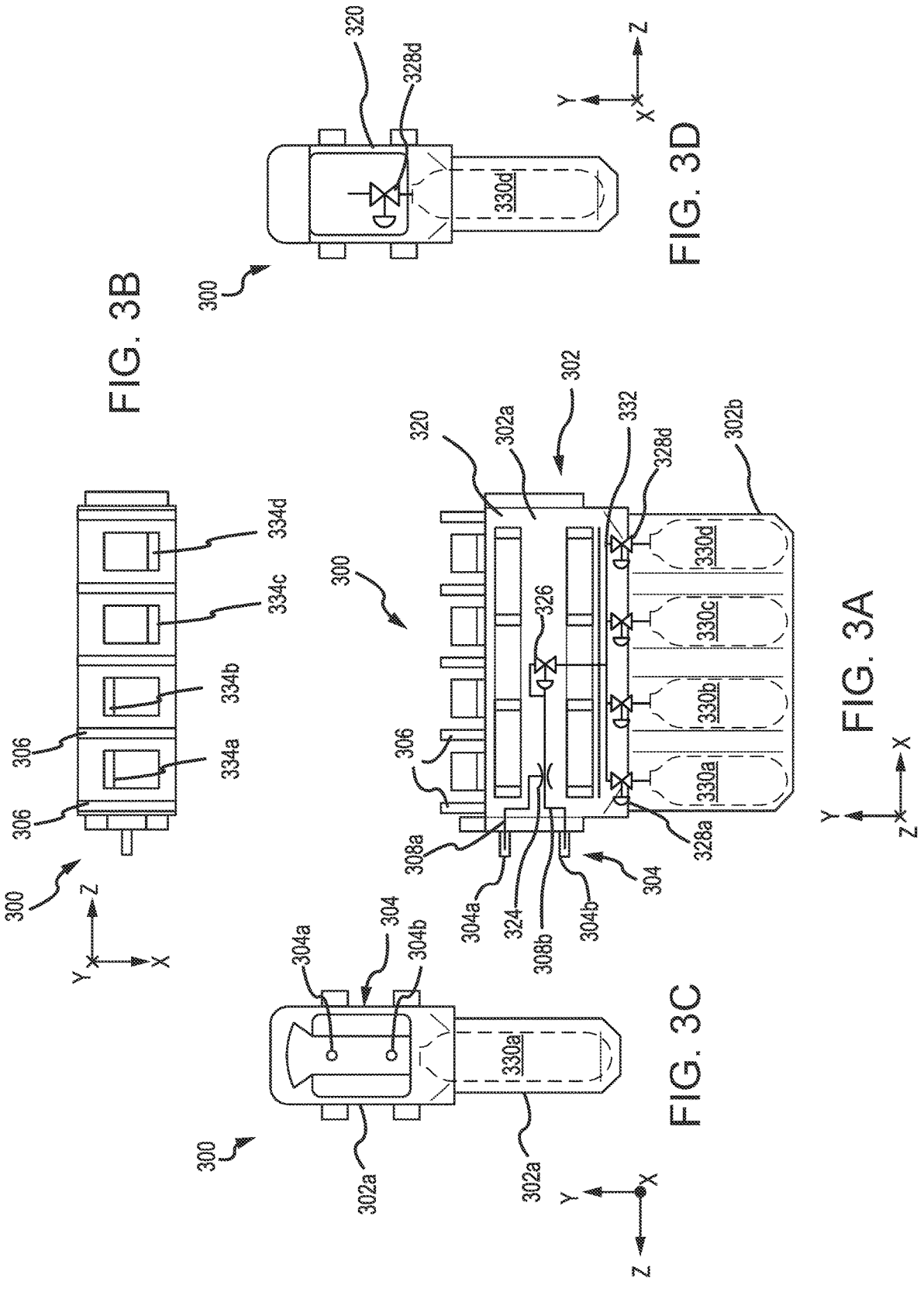
FIGS. 3A, 3B, 3C, and 3D illustrate an integrated pressure regulator and ejector pump, in accordance with various embodiments.

Referring now to FIG. 2, a functional diagram 200 of a urinary relief system is illustrated, in accordance with various embodiments. Functional diagram 200 may be an example of urinary relief system 100 described above with respect to FIGS. 1A and 1B. Functional diagram 200 includes a collection device 204, a storage device 206, and a control device 208. In various embodiments, collection device 204, storage device 206, and control device 208 may be examples of human interface device 104, storage unit 106, and control unit 108, respectively, described above with respect to FIGS. 1A and 1B.

Collection device 204 is configured to collect liquid (e.g., urine) from a user (e.g., pilot 102). Collection device 204 has an outlet port 204a, storage device 206 has a storage inlet port 206a and a storage outlet port 206b, and control device 208 has a control inlet port 208a and a control outlet port 208b. Outlet port 204a of collection device 204 is configured to transfer the collected liquid from collection device 204 to storage device 206. Outlet port 204a of collection device 204 is connected to storage inlet port 206a of storage device 206. Storage outlet port 206b of storage device 206 is connected to control inlet port 208a of control device 208. In various embodiments, a hose, or tube, may be used to make the connection between outlet and inlet ports. In various embodiments, there is a first quick connector interface 212 between collection device 204 and storage device 206 that allows for quick and simple attachment and detachment of a hose, or tube. In various embodiments, there is a second quick connector interface 214 between storage device 206 and control device 208 that allows for quick and simple attachment and detachment the hose, or tube. In various embodiments, a filter, or flow restrictor 210, is connected to storage outlet port 206b of storage device 206. Flow restrictor 210 prevents liquid (e.g., urine) from passing to control device 208 while allowing air to pass to control device 208.

Control device 208 includes an ejector head 220 and a pressurized gas supply 222. Ejector head 220 includes houses control inlet port 208a, control outlet port 208b, an ejector 224, and a pressure regulator 226. Ejector 224 is coupled to pressure regulator 226, control inlet port 208a, and control outlet port 208b. Pressurized gas supply 222 includes a first valve 228a, a second valve 228b, a third valve 228c, a first $CO_2$ cartridge 230a, a second $CO_2$ cartridge 230b, and a third $CO_2$ cartridge 230c. First $CO_2$ cartridge 230a is coupled to first valve 228a, second $CO_2$ cartridge 230b is coupled to second valve 228b, and third $CO_2$ cartridge 230c is coupled to third valve 228c. First valve 228a, second valve 228b, and third valve 228c are connected in parallel to pressure regulator 226 by a high pressure line 232. That is, each valve 228a, 228b, 228c has an independent high pressure connection to high pressure line 232 that is in turn connected to pressure regulator 226. While the description herein uses $CO_2$ cartridges, it should be appreciated that any suitable pressurized gas container may be used.

Each $CO_2$ cartridge 230a, 230b, 230c is sealed and connected to the corresponding valve 228a, 228b, 228c. Each valve 228a, 228b, 228c performs the same function. For example, first valve 228a is configured to puncture the seal of first $CO_2$ cartridge 230a, in response to an input, allowing the compressed air in first $CO_2$ cartridge 230a to pass through first valve 228a, into high pressure line 232, and to pressure regulator 226. Second valve 228b is configured to puncture the seal of second $CO_2$ cartridge 230b, in response to an input, allowing the compressed air in second $CO_2$ cartridge 230b to pass through second valve 228b, into high pressure line 232, and to pressure regulator 226. Third valve 228c is configured to puncture the seal of third $CO_2$ cartridge 230c, in response to an input, allowing the compressed air in third $CO_2$ cartridge 230c to pass through third valve 228c, into high pressure line 232, and to pressure regulator 226.

Pressure regulator 226 has a high pressure inlet 226a and a reduced pressure outlet 226b. Pressure regulator 226 receives the high pressure air from high pressure line 232 at high pressure inlet 226a, reduces the pressure of the air (e.g., $CO_2$), and outputs the air at a reduced pressure from reduced pressure outlet 226b. The pressure of the air at reduced pressure outlet 226b is about 15 times to about 45 times less than the pressure of the air received at high pressure inlet 226a. In various embodiments, the pressure of the air at reduced pressure outlet 226b is about 25 times to about 35 times less than the pressure of the air received at high pressure inlet 226a. Reducing the pressure of the air by pressure regulator 226 slows the release of the pressurized air (e.g., $CO_2$) and therefore extends the lifespan of each $CO_2$ cartridge 230a, 266b, 226c. Adjusting the release pressure (e.g., air pressure at reduced pressure outlet 226b) either up or down may decrease or increase, respectively, the effective lifespan of each $CO_2$ cartridge 230a, 230b, 230c.

Ejector 224 has an air inlet 224a, an air outlet 224b, and a vacuum port 224c. Air inlet 224a of ejector 224 is connected to reduced pressure outlet 226b of pressure regulator 226. Air outlet 224b is connected to control outlet port 208b which is open to the environment (e.g., cockpit, cabin, etc.). Vacuum port 224c is connected to storage outlet port 206b of storage device 206. Ejector 224 receives pressurized air at air inlet 224a and passes the pressurized air to air outlet 224b to create a vacuum at vacuum port 224c. The vacuum creates a motive force that passes through storage device 206 to collection device 204 and draws, or sucks, air and liquid (e.g., urine) from collection device 204 into storage device 206. A combination of the materials inside storage device 206 and flow restrictor 210 trap and prevent the liquid from being pulled to ejector head 220, and more specifically, into ejector 224. Instead, any air present in the system is drawn by the vacuum created by ejector 224, continuing to pull liquid from collection device 204.

Referring now to FIGS. 3A-3D, a control unit 300 is illustrated, in accordance with various embodiments. Control unit 300 may be an example of control device 208 described above with respect to FIG. 2. Control unit 300 includes similar components to those describe above with respect to control device 208 in FIG. 2, including an ejector head 320, a pressurized gas supply 322, a control inlet port 308a, a control outlet port 308b, an ejector 324, a pressure regulator 326, a first valve 328a, a second valve 328b, a third valve 328c, a first $CO_2$ cartridge 330a, a second $CO_2$ cartridge 330b, and a third $CO_2$ cartridge 330c. These components are described above with respect to FIG. 2, the description of which may not be repeated below. Control unit 300 further includes a housing 302, a fast connector 304, a fourth valve 328d, a fourth $CO_2$ cartridge 330c, a first toggle 334a, a second toggle 334b, a third toggle 334b, a fourth toggle 334d.

Housing 302 includes an upper portion 302a and a lower portion 302b that may be detachable from upper portion 302a. Upper portion 302a houses ejector head 320 including control inlet port 308a, control outlet port 308b, ejector 324, and pressure regulator 326. Lower portion 302b encloses valves 328a-328d and $CO_2$ cartridges 330a-330d. In various embodiments, lower portion 302b may be coupled to upper portion 302a using snaps, buttons, friction retainers, or press fitting, among others. In various embodiments, lower portion 302b may be coupled to upper portion 302a by sliding a feature of lower portion 302b into a feature of upper portion 302a, such as rails for example. A high pressure line 332 connects valves 328a-328d to ejector head 320, and more specifically, to pressure regulator 326. Toggles 334a-334d are coupled to upper portion 302a and are configured to engage valves 328a-328d individually. In various embodiments, housing 302 may further include finger guards 306 disposed between and separating each of the toggles 334a-334d.

Fast connector 304 includes a first port 304a and a second port 304b. Fast connector 304 is removable from housing 302 and is configured to quickly attach to and detach from housing 302 at attachment point 336. When fast connector 304 is attached to housing 302, first port 304a is aligned with control inlet port 308a and second port 304b is aligned with control outlet port 308b. A hose, tube, or other connector, may be connected to first port 304a at one end a storage device (e.g., storage device 206) at an opposite end. In various embodiments, a hose, tube, or other connector, may be connected to second port 304b to control how air is vented from control unit 300.

Each toggle 334a-334d is configured to engage a corresponding valve 328a-328d. Each toggle 334a-334d is configured to toggle between an engaged position and a disengaged position. Each toggle 334a-334d is initialized in the disengaged position (e.g., first toggle 334a and second toggle 334b). Each toggle 334a-334d may be individually flipped, or switched, to the engaged position (e.g., third toggle 334c and fourth toggle 334d). Toggles 334a-334d are configured to provide tactile and/or audible feedback to the user (e.g., pilot 102), such as a click, allowing the user to know the toggle was engaged without looking. Each toggle 334a-334d has a length L1 that allows the user (e.g., pilot 102) to feel and activate, or switch, toggle 334a-334d without looking. Length L1 may be about 0.25 inches to about 1 inch, and more specifically, about 0.4 inches to about 0.6 inches. Flipping toggle 334a-334d from the disengaged position to the engage position opens the corresponding valve 328a-328d.

Opening each valve 328a-328d punctures the corresponding $CO_2$ cartridge 330a-330d releasing the pressurized air and activating control unit 300. In various embodiments, valves 328a-328d may be configured to open and stay opened, allowing all of the gas of each $CO_2$ cartridge 330a-330d be used. In various embodiments, valves 328a-328d may be configured to open and close, allowing the user (e.g., pilot 102) to the control the gas used from each $CO_2$ cartridge 330a-330d, allowing for multiple using one or more $CO_2$ cartridges 330a-330d more than once.

Lower portion 302b may be removed from upper portion 302a to remove and replace spent $CO_2$ cartridges 330a-330d. After removing lower portion 302b, each $CO_2$ cartridge 330a-330d is removed and replaced. Each toggle 334a-334d is moved, or switched, back to the disengaged position. Lower portion 302b may then be reconnected to upper portion 302a. In various embodiments, this may be accomplished while control unit 300 is connected to a storage device (e.g., storage device 206).

Figure 4:
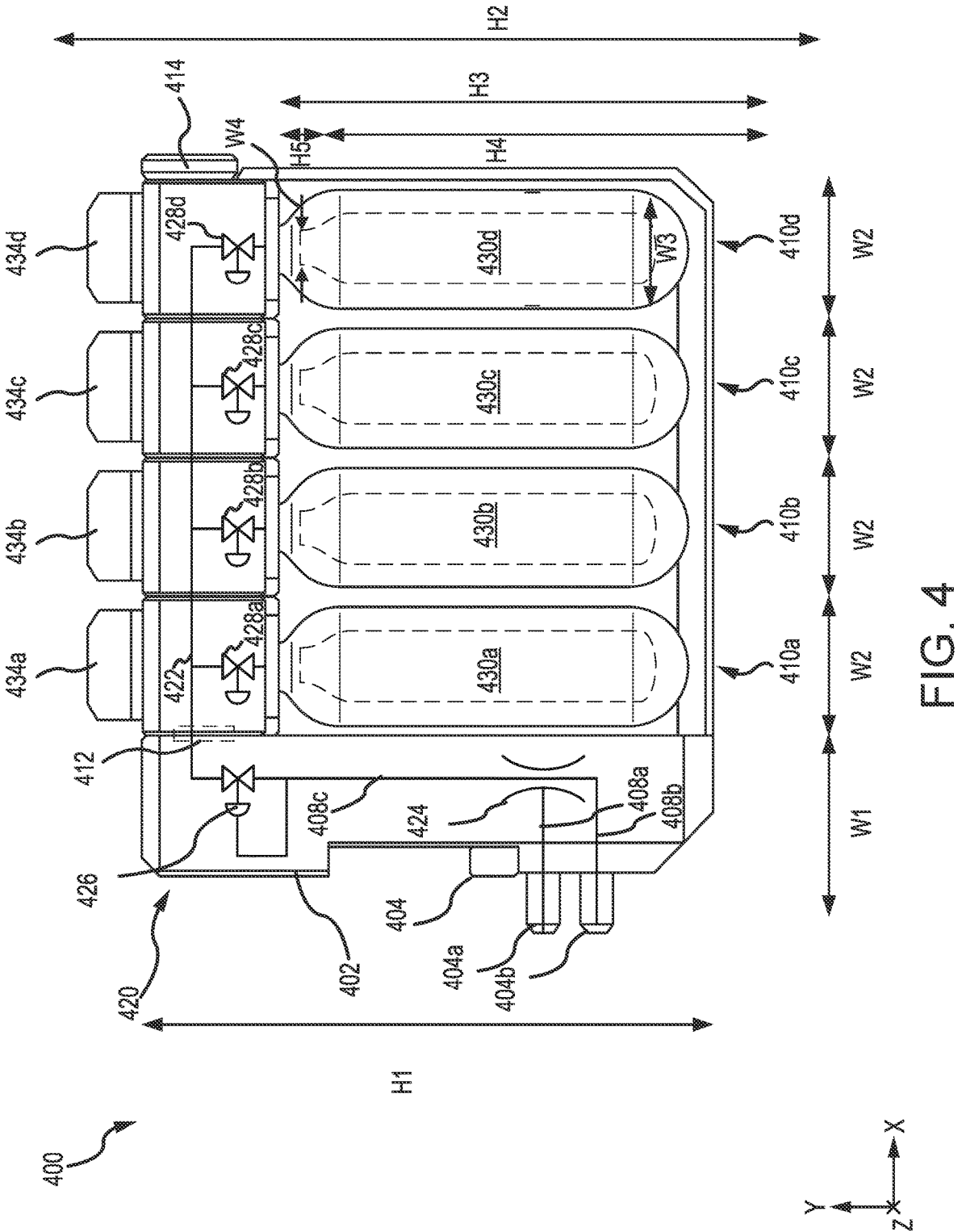
FIG. 4 illustrates an integrated pressure regulator and ejector pump, in accordance with various embodiments.

Referring now to FIG. 4, a control unit 400 is illustrated, in accordance with various embodiments. Control unit 400 may be an example of control device 208 described above with respect to FIG. 2. Control unit 400 includes similar components to those describe above with respect to control unit 300 in FIG. 3, including an ejector head 420, a pressurized gas supply 422, a control inlet port 408a, a control outlet port 408b, an ejector 424, a pressure regulator 426, a first valve 428a, a second valve 428b, a third valve 428c, a fourth valve 428d, a first $CO_2$ cartridge 430a, a second $CO_2$ cartridge 430b, and a third $CO_2$ cartridge 430c, a fourth $CO_2$ cartridge 430d, a first toggle 434a, a second toggle 434b, a third toggle 434c, a fourth toggle 434d, and a fast connector 404. These components are described above with respect to FIG. 3, the description of which may not be repeated below. Control unit 400 further includes an ejector head housing 402, a first cartridge housing 410a, a second cartridge housing 410b, a third cartridge housing 410c, and a fourth cartridge housing 410d.

Ejector head housing 402 encloses control inlet port 408a, control outlet port 408b, a control high pressure port 408c, ejector 424, and pressure regulator 426. Fast connector 404 is removably connected to ejector head housing 402 over control inlet port 408a and control inlet port 408b. Fast connector 404 has a first port 404a and a second port 404b. When fast connector 404 is connected to ejector head housing 402, first port 404a is in communication with control inlet port 408a and second port 404b is in communication with control inlet port 408b.

Ejector head housing 402 has a height H1 (e.g., in the y-direction) and a width W1 (e.g., in the x-direction). Height H1 is about 3.5 inches to about 6 inches, and more specifically, about 4 inches to about 5 inches. Width W1 is about 1 inch to about 2.5 inches, and more specifically, about 1.25 inches to about 2 inches.

Each cartridge housing 410a-410d encloses a corresponding valve 428a-428d and a corresponding $CO_2$ cartridge 430a-430d. Each cartridge housing 410a-410d further includes a corresponding toggle 434a-434d configured to engage the corresponding valve 428a-428d. Cartridge housing 410a-410d has a height H2 (e.g., in the y-direction) and a width W2 (e.g., in the x-direction). Height H2 is about 4 inches to about 7 inches, and more specifically, about 4.5 inches to about 6 inches. Width W2 is about 1 inch to about 2 inches, and more specifically, about 1.25 inches to about 1.75 inches.

$CO_2$ cartridge 430a-430d is sized to fit within cartridge housing 410a-410d having a total height H3, a body height H4, a neck height H5, a body width W3, and a neck width W4. Height H3 is about 3.75 inches to about 5.25 inches and more specifically, about 3.5 inches. Body height H4 is about 3.5 inches to about 4.5 inches and more specifically, about 3 inches. Neck height H5 is about 0.25 inches to about 0.75 inches, and more specifically, about 0.5 inches. Body width W3 is about 0.4 inches to about 1 inch, and more specifically, about 0.6 inches to about 0.8 inches. Neck width W4 is about 0.25 inches to about 0.5 inches, and more specifically, about 0.375 inches.

Cartridge housing 410*a*-410*d* further includes a first connector 412 and a second connector 414. First connector 412 of each cartridge housing 410*a*-410*d* is configured to engage second connector 414 of ejector head housing 402 and/or cartridge housing 410*a*-410*d*. In various embodiments, first connector 412 may be press fit onto second connector 414. In various embodiments, first connector 412 may slide onto second connector 414. In various embodiments, an O-ring may be used to provide an air tight seal between first connector 412 and second connector 414. Connections between first connector 412 and second connector 414 forms a high pressure line 432.

This configuration allows control unit 400 to be modular. That is, ejector head housing 402 may be connected to one or more cartridge housings 410*a*-410*d*. This allows the user (e.g., pilot 102) to attach as many cartridge housings 410*a*-410*d* as will be used during a specific mission. The user may choose different numbers of cartridge housings 410*a*-410*d* for size, weight, and/or number of uses anticipated for a mission. Additionally, this allows for reloading control unit 400 by swapping cartridge housings 410*a*-410*d*.

Benefits, other advantages, and solutions to problems have been described herein with regard to specific embodiments. Furthermore, the connecting lines shown in the various figures contained herein are intended to represent exemplary functional relationships and/or physical couplings between the various elements. It should be noted that many alternative or additional functional relationships or physical connections may be present in a practical system. However, the benefits, advantages, solutions to problems, and any elements that may cause any benefit, advantage, or solution to occur or become more pronounced are not to be construed as critical, required, or essential features or elements of the disclosure. The scope of the disclosure is accordingly to be limited by nothing other than the appended claims, in which reference to an element in the singular is not intended to mean "one and only one" unless explicitly so stated, but rather "one or more." Moreover, where a phrase similar to "at least one of A, B, or C" is used in the claims, it is intended that the phrase be interpreted to mean that A alone may be present in an embodiment, B alone may be present in an embodiment, C alone may be present in an embodiment, or that any combination of the elements A, B and C may be present in a single embodiment; for example, A and B, A and C, B and C, or A and B and C. Different cross-hatching is used throughout the figures to denote different parts but not necessarily to denote the same or different materials.

Systems, methods and apparatus are provided herein. In the detailed description herein, references to "one embodiment," "an embodiment," "various embodiments," etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described. After reading the description, it will be apparent to one skilled in the relevant art(s) how to implement the disclosure in alternative embodiments.

Numbers, percentages, or other values stated herein are intended to include that value, and also other values that are about or approximately equal to the stated value, as would be appreciated by one of ordinary skill in the art encompassed by various embodiments of the present disclosure. A stated value should therefore be interpreted broadly enough to encompass values that are at least close enough to the stated value to perform a desired function or achieve a desired result. The stated values include at least the variation to be expected in a suitable industrial process, and may include values that are within 5% of a stated value. Additionally, the terms "substantially," "about" or "approximately" as used herein represent an amount close to the stated amount that still performs a desired function or achieves a desired result. For example, the term "substantially," "about" or "approximately" may refer to an amount that is within 5% of a stated amount or value.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises," "comprising," or any other variation thereof, are intended to cover a non-exclusive inclusion, such that a process, method, article, or apparatus that comprises a list of elements does not include only those elements but may include other elements not expressly listed or inherent to such process, method, article, or apparatus.

Finally, it should be understood that any of the above-described concepts can be used alone or in combination with any or all of the other above-described concepts. Although various embodiments have been disclosed and described, one of ordinary skill in this art would recognize that certain modifications would come within the scope of this disclosure. Accordingly, the description is not intended to be exhaustive or to limit the principles described or illustrated herein to any precise form. Many modifications and variations are possible in light of the above teaching.

What is claimed is:

1. A control unit for a urinary relief system, comprising:
   a pressure regulator having a high pressure inlet and a reduced pressure outlet, the high pressure inlet having a first air pressure, and the reduced pressure outlet having a second air pressure;
   an ejector having a pressurized air input, a vacuum port, and an air output, the pressurized air input of the ejector coupled to the reduced pressure outlet of the pressure regulator and the vacuum port connected to an outlet port of a storage device;
   an ejector head housing the pressure regulator and the ejector; and
   a pressurized gas source coupled to the high pressure inlet of the pressure regulator, the pressurized gas source providing an air flow having the first air pressure.

2. The control unit of claim 1, wherein the second air pressure is about 25 times less than the first air pressure to about 35 times less than the first air pressure.

3. The control unit of claim 1, further comprising:
   a valve disposed between the pressurized gas source and the pressure regulator, the valve configured to pass a gas from the pressurized gas source to the pressure regulator.

4. The control unit of claim 3, further comprising:
   a toggle coupled to the valve, the toggle configured to activate the valve to release the gas from the pressurized gas source.

5. The control unit of claim 4, wherein the toggle is further configured to deactivate the valve, stopping the release of the gas from the pressurized gas source.

6. The control unit of claim 1, wherein the pressurized gas source includes one or more $CO_2$ cartridges.

7. The control unit of claim 6, further comprising:

one or more valves, each of the one or more valves being disposed between each $CO_2$ cartridge of the one or more $CO_2$ cartridges and the pressure regulator, each valve configured to pass pressurized $CO_2$ from each $CO_2$ cartridge to the pressurized gas source.

8. A urinary relief system, comprising:

a human interface device;

a storage device having an inlet port and an outlet port, the storage device coupled to the human interface device via the inlet port; and a control unit coupled to the storage device via the outlet port, the control unit including:

a pressure regulator having a high pressure inlet and a reduced pressure outlet, the high pressure inlet having a first air pressure, and the reduced pressure outlet has a second air pressure;

an ejector having a pressurized air input, a vacuum port, and an air output, the pressurized air input of the ejector coupled to the reduced pressure outlet of the pressure regulator and the vacuum port connected to the storage device;

an ejector head housing the pressure regulator and the ejector; and a pressurized gas source coupled to the high pressure inlet of the pressure regulator, the pressurized gas source providing an air flow having the first air pressure.

9. The urinary relief system of claim 8, the control unit further comprising:

an air inlet port coupled to the ejector and to the storage device; and an air outlet port coupled to the ejector.

10. The urinary relief system of claim 9, further comprising a flow restrictor coupled between the storage inlet port and the storage outlet port and wherein the control unit further comprises:

a connector having a first port and a second port, the connector configured to be removably coupled to the ejector head housing such that the first port is coupled to the air inlet port and the second port is coupled to the air outlet port.

11. The urinary relief system of claim 8, wherein the second air pressure is about 30 times less than the first air pressure.

12. The urinary relief system of claim 8, the control unit further comprising:

a pressurized gas housing to house the pressurized gas source, the pressurized gas housing configured to be removably coupled to the ejector head housing.

13. The urinary relief system of claim 8, the control unit further comprising:

a valve disposed between the pressurized gas source and the pressure regulator, the valve configured to pass a gas from the pressurized gas source to the pressure regulator.

14. The urinary relief system of claim 8, wherein the pressurized gas source includes one or more $CO_2$ cartridges.

15. A urinary relief system, comprising:

a human interface device;

a storage device having an inlet port and an outlet port, the storage device coupled to the human interface device via the inlet port; and a control unit coupled to the storage device via the outlet port, the control unit including:

an ejector head housing having an air inlet port and an air outlet port, the air inlet port coupled to the storage device;

a first pressurized gas housing removably coupled to the ejector head housing;

a first pressurized gas source disposed in the first pressurized gas housing;

a pressure regulator disposed in the ejector head housing, the pressure regulator coupled to the first pressurized gas source; and an ejector coupled to the pressure regulator, the air inlet port, and the air outlet port.

16. The urinary relief system of claim 15, wherein the pressure regulator includes a high pressure inlet receiving a gas having a first pressure and a reduced pressure outlet outputting the gas having a second pressure that is less than the first pressure.

17. The urinary relief system of claim 16, wherein the second pressure is about 15 times less than the first pressure to about 45 times less than the first pressure.

18. The urinary relief system of claim 15, further comprising:

a second pressurized gas housing removably coupled to the first pressurized gas housing; and a second pressurized gas source disposed in the second pressurized gas housing.

19. The urinary relief system of claim 15, the first pressurized gas housing further comprising:

a first valve coupled to the first pressurized gas source and to the pressure regulator when the first pressurized gas housing is coupled to the ejector head housing; and a first toggle disposed on an outside surface of the first pressurized gas housing, the first toggle coupled to the first valve and configured to open the first valve in response to being toggled.

20. The urinary relief system of claim 15, wherein the first pressurized gas housing is configured to allow replacing the first pressurized gas source.

\* \* \* \* \*